United States Patent
Otsuki et al.

(10) Patent No.: US 8,161,794 B2
(45) Date of Patent: Apr. 24, 2012

(54) SULFUR COMPONENT DETECTING DEVICE

(75) Inventors: Hiroshi Otsuki, Susono (JP); Takamitsu Asanuma, Mishima (JP); Kohei Yoshida, Gotenba (JP); Hiromasa Nishioka, Susono (JP); Shinya Hirota, Susono (JP); Kotaro Hayashi, Mishima (JP)

(73) Assignee: Toyota Jidosha Kabushiki Kaisha, Toyota (JP)

( * ) Notice: Subject to any disclaimer, the term of this patent is extended or adjusted under 35 U.S.C. 154(b) by 393 days.

(21) Appl. No.: 12/310,571

(22) PCT Filed: Jan. 17, 2008

(86) PCT No.: PCT/JP2008/050921
§ 371 (c)(1),
(2), (4) Date: Feb. 27, 2009

(87) PCT Pub. No.: WO2008/088072
PCT Pub. Date: Jul. 24, 2008

(65) Prior Publication Data
US 2010/0095741 A1    Apr. 22, 2010

(30) Foreign Application Priority Data
Jan. 17, 2007 (JP) .................... 2007-008047

(51) Int. Cl.
*G01N 27/12* (2006.01)
(52) U.S. Cl. ..................................... 73/23.31
(58) Field of Classification Search .......... None
See application file for complete search history.

(56) References Cited

U.S. PATENT DOCUMENTS

| | | | | |
|---|---|---|---|---|
| 4,715,944 A | * | 12/1987 | Yanagida et al. | 204/426 |
| 5,397,442 A | * | 3/1995 | Wachsman | 205/781 |
| 6,756,016 B2 | * | 6/2004 | Miller et al. | 422/98 |
| 2004/0063215 A1 | * | 4/2004 | Horiuchi et al. | 436/121 |
| 2006/0064969 A1 | | 3/2006 | Yoshida et al. | |
| 2006/0186901 A1 | | 8/2006 | Itakura et al. | |

FOREIGN PATENT DOCUMENTS

| | | |
|---|---|---|
| CN | 1285914 A | 2/2001 |
| CN | 1825103 A | 8/2006 |
| EP | 1 431 756 A1 | 6/2004 |
| GB | A-2-198-844 | 6/1988 |
| JP | A-62-192643 | 8/1987 |
| JP | A 09-152394 | 6/1997 |
| JP | A-2000-320323 | 11/2000 |
| JP | A-2004-239706 | 8/2004 |
| JP | A-2005-133610 | 5/2005 |
| WO | WO 99/34199 A1 | 7/1999 |
| WO | WO 03/029801 A1 | 4/2003 |

OTHER PUBLICATIONS

European Search Report issued Mar. 9, 2011 in European Patent Application No. 08703751.1.
Office Action issued in Chinese Patent Appln. No. 200880001244.4; mailed Jan. 18, 2012.

* cited by examiner

*Primary Examiner* — Hezron E Williams
*Assistant Examiner* — Mark A Shabman
(74) *Attorney, Agent, or Firm* — Oliff & Berridge, PLC (57) ABSTRACT

A metal or metal compound able to trap a sulfur component in exhaust gas is arranged in a flow passage of exhaust gas in an internal combustion engine. When the amount of sulfur component trapped in the metal or metal compound increases over the passage of time, a property of the metal or metal compound which changes along with the increase in the amount of trapped sulfur component is measured and the sulfur component in the gas is detected from the measured property.

21 Claims, 7 Drawing Sheets

$Ba(NO_3)_2$  $Ba(NO_3)_2$           $BaSO_4$  $BaSO_4$
$Ba(NO_3)_2$  $Ba(NO_3)_2$    ⇒    $BaSO_4$  $BaSO_4$
$Ba(NO_3)_2$  $Ba(NO_3)_2$           $Ba(NO_3)_2$  $Ba(NO_3)_2$
$Ba(NO_3)_2$  $Ba(NO_3)_2$           $BaSO_4$  $BaSO_4$

(C)

PdO PdO PdO          PdS PdS PdS
PdO PdO PdO    ⇒    PdS PdO
PdO PdO PdO          PdS PdO PdS

Fig.8

SULFUR COMPONENT DETECTING DEVICE

TECHNICAL FIELD

The present invention relates to a sulfur component detecting device.

BACKGROUND ART $SO_x$ concentration sensors for detecting the $SO_x$ concentration in exhaust gas have been known since the past. These known $SO_x$ concentration sensors normally use a solid electrolyte and are designed to measure the electromotive force generated by the change of $SO_x$ to sulfate ions so as to detect the $SO_x$ concentration in the exhaust gas (for example, refer to Japanese Patent Publication (A) No. 2004-239706).

However, there are the large problems that a conventional sulfur component detecting device using such an $SO_x$ concentration sensor will work only under high temperatures, the device becomes bulky, and in particular when the $SO_x$ concentration is low, it cannot detect the $SO_x$ concentration. Conventionally, as in this $SO_x$ concentration sensor, attention has been directed only at instantaneously detecting the $SO_x$ concentration. So long as trying to instantaneously detect the $SO_x$ concentration in such a way, various problems such as explained above will inevitably occur.

The inventors changed their thinking and turned their gaze to not instantaneously detecting the $SO_x$ concentration, but to detecting the cumulative amount of $SO_x$ exhausted over a long period. By changing their thinking in this way, they learned that it is possible to easily detect the amount of $SO_x$ in the exhaust gas—though the cumulative amount of $SO_x$ exhausted over a long period of time.

Note that the present invention may be applied most appropriately when detection of a cumulative amount of $SO_x$ exhausted over a long period of time is demanded. Further, even though it is unable to detect instant $SO_x$ concentrations, the present invention may be applied in cases where it is sufficient to be able to detect an average value of $SO_x$ concentration within a given fixed period or an average value of an exhausted amount of $SO_x$ in a given fixed period.

DISCLOSURE OF THE INVENTION

An object of the present invention is to provide a sulfur component detecting device capable of easily detecting a sulfur component in a gas.

According to the present invention, there is provided a sulfur component detecting device for detecting a sulfur component contained in a flowing gas, wherein a metal or metal compound able to trap a sulfur component in a gas is arranged in a gas flow passage, when an amount of the sulfur component trapped at the metal or metal compound increases along with the passage of time, a property of the metal or metal compound changing along with the increase in the amount of the trapped sulfur component is measured, and the sulfur component in the gas is detected from the measured property.

BEST MODE FOR CARRYING OUT THE INVENTION

Figure 1:
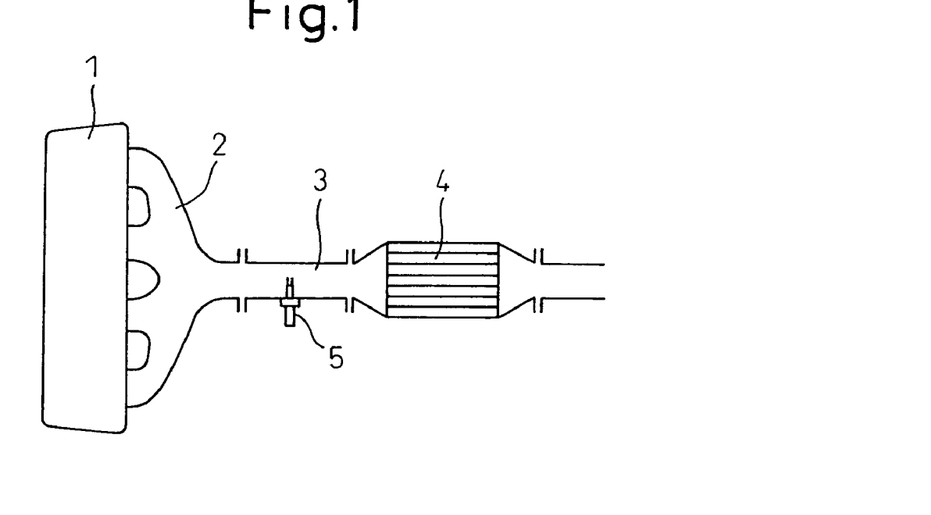
FIG. 1 is a view showing a compression ignition type internal combustion engine.

FIG. 1 shows a case of applying the present invention to a compression ignition type internal combustion engine. Referring to FIG. 1, 1 indicates an engine body, 2 an exhaust manifold, 3 an exhaust pipe, 4 an $NO_x$ storage reduction catalyst or other catalyst, and 5 an $SO_x$ sensor arranged in an exhaust gas passage in an exhaust pipe 3 for detecting a sulfur component contained exhaust gas, that is, $SO_x$.

Note that, the present invention not only may be applied to detection of the $SO_x$ in exhaust gas from an internal combustion engine, but may also be applied to, for example, detection of a sulfur component of exhaust gas from a factory or the like. That is, the present invention may be applied to detection of a sulfur component in gas in all sorts of technical fields. However, below, as shown below in FIG. 1, the present invention will be explained taking as an example the case of application to detection of a sulfur component in exhaust gas from an internal combustion engine.

Figure 2:
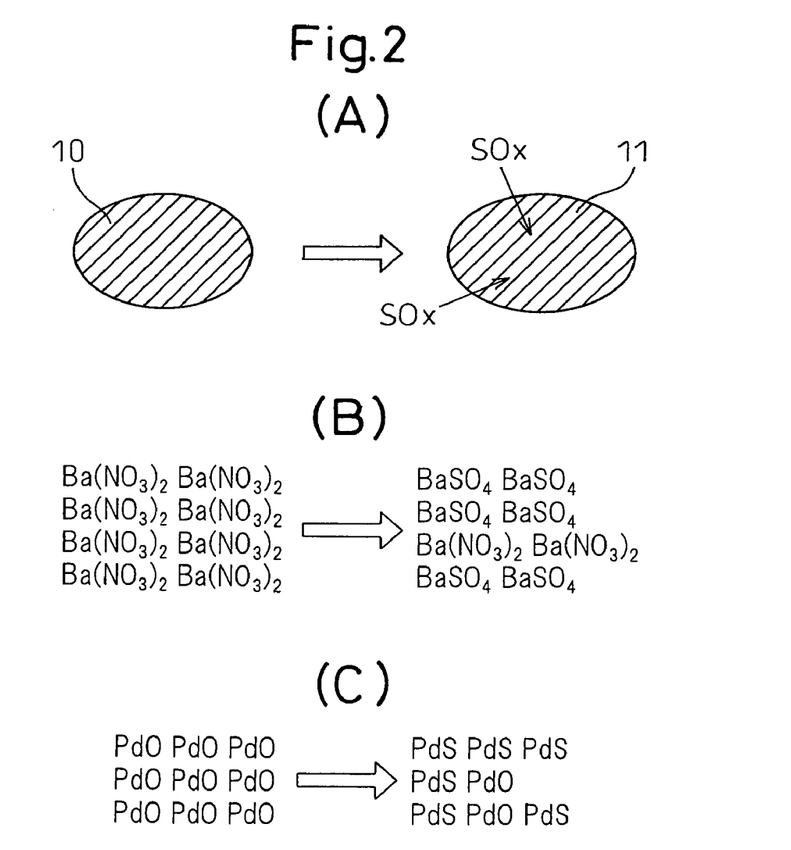
FIG. 2 is a view for explaining the principle of detection of a sulfur component.

FIG. 2 shows a principle of detection of a sulfur component according to the present invention. In the present invention, a metal or metal compound able to trap the sulfur component in a gas is arranged in the gas flow passage. In the embodiment shown in FIG. 1, a metal or metal compound able to trap $SO_x$ in exhaust gas is arranged in the exhaust gas flow passage. This metal or metal compound is schematically shown in FIG. 2(A) with the reference numeral 10. The metal or metal compound 10 shown in FIG. 2(A) comprises a non-sulfur-containing metal or metal compound. According to an embodiment of the present invention, this metal or metal compound 10 comprises an alkali metal, alkali earth metal, rare earth metal, precious metal, or compounds of these metals.

Next, the detection method of a sulfur component will be explained taking the example of the case of using barium Ba, which is one alkali earth metal, or a compound of barium Ba as the metal or metal compound 10.

Barium Ba becomes barium oxide BaO in the atmosphere. This barium oxide BaO, when placed in the exhaust gas, immediately is changed to barium carbonate $BaCO_3$ due to the CO and $CO_2$ contained the exhaust gas. Further, this barium carbonate $BaCO_3$ changes to barium nitrate $Ba(NO_3)_2$ due to the $NO_x$ contained in the exhaust gas.

That is, when barium Ba is used, the metal or metal compound 10 shown in FIG. 2(A) is barium oxide BaO, barium carbonate $BaCO_3$, or barium nitrate $Ba(NO_3)_2$. When this metal or metal compound 10 is placed in the exhaust gas, it becomes barium nitrate $Ba(NO_3)_2$. Expressed generally, the metal or metal compound 10 shown in FIG. 2(A) comprises an oxide or carbonate or nitrate. When this metal or metal compound 10 is placed in the exhaust gas, it becomes a nitrate.

On the other hand, exhaust gas contains a sulfur component, that is, $SO_x$, though in a smaller amount compared to the CO, HC, or $NO_x$. This $SO_x$ is trapped by the metal or metal compound 10 and, as shown in FIG. 2(A), changes to a sulfur-containing metal compound 11. When barium Ba is used, this sulfur-containing metal compound 11 is barium sulfate $BaSO_4$. Accordingly, when the metal or metal compound 10 is placed in the exhaust gas, as shown in FIG. 2(B), the barium nitrate $Ba(NO_3)_2$ forming part of the metal compound 10 comprising barium nitrate $Ba(NO_3)_2$ changes to barium sulfate $BaSO_4$. Expressed generally, a portion of the nitrate changes to a sulfate. In this case, the ratio of the sulfate in the metal compound 11 becomes higher along with the passage of time, that is, the more the amount of the trapped sulfur component increases.

On the other hand, FIG. 2(C) shows a case where the metal or metal compound 10 comprises a precious metal or its compound. As this precious metal, palladium Pd, rhodium Rh, or platinum Pt may be used. FIG. 2(C) shows a case of using palladium Pd as an example. In this case, if a sulfur component is trapped, the metal oxide PdO changes to a sulfide PdS.

If the nitrate changes to a sulfate or if the metal oxide changes to a sulfide, it will change in properties. Accordingly, the amount of the trapped sulfur component, that is, the amount of sulfur component in the gas, can be estimated from the change of a property. Therefore, in the present invention, when a non-sulfur-containing metal or metal compound 10 changes to a sulfur-containing metal compound 11 along with the passage of time, a property of the metal compound 11 is measured and the sulfur component in the gas is detected from the measured property.

That is, in the present invention, in a different manner of speaking, when the amount of sulfur component trapped at the metal or metal compound 10 increases along with the passage of time, a property of the metal or metal compound 10 changing along with the increase of the amount of trapped sulfur component is measured and the sulfur component in the gas is detected from the measured property.

Next, referring to FIG. 3 to FIG. 8, the property to be measured and a detection method corresponding to the property to be measured will be explained. Note that, FIG. 3 to FIG. 8 will be explained taking as a example the case of a nitrate changing to a sulfate as shown in FIG. 2(B).

Figure 3:
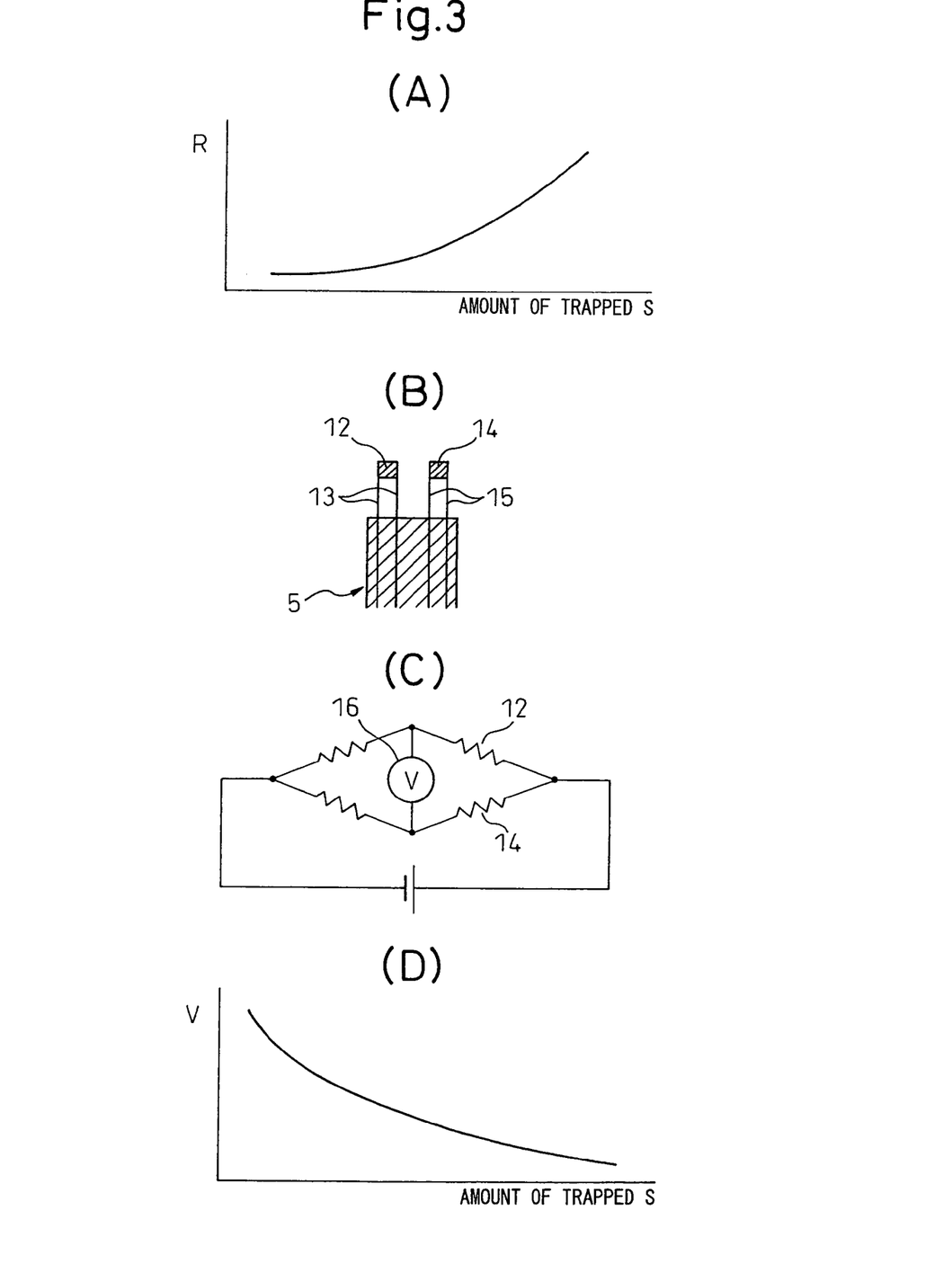
FIG. 3 is a view for explaining a method of detection of a sulfur component.
Figure 4:
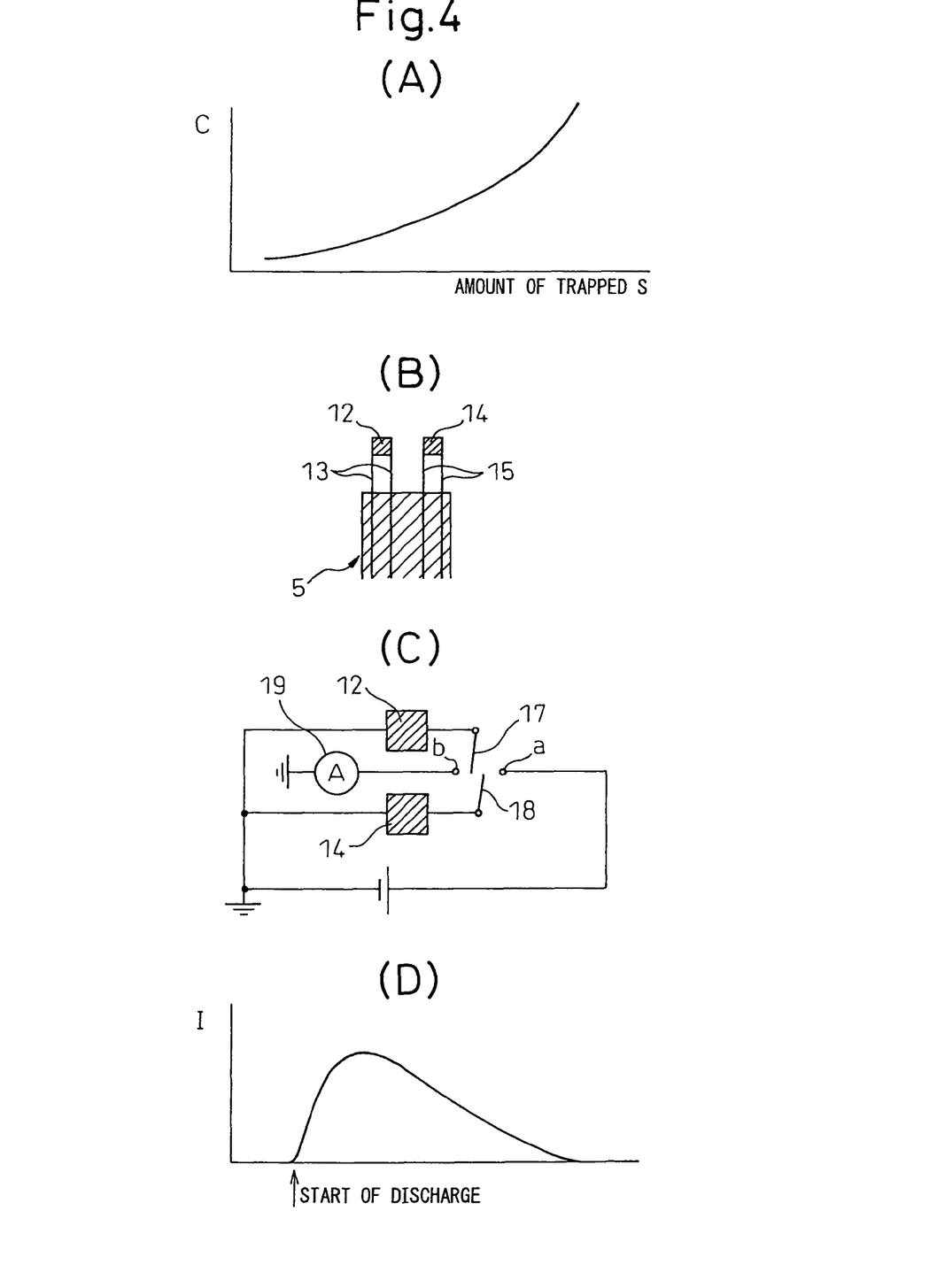
FIG. 4 is a view for explaining the method of detection of a sulfur component.

FIG. 3 and FIG. 4 show a case where the property to be measured is an electrical property, and FIG. 3 shows a case where the measured electrical property is the electrical resistance.

FIG. 3(A) shows the relationship of the amount of trapped sulfur S and the electrical resistance R. As shown in FIG. 3(A), the more the amount of trapped sulfur S increases, that is, the greater the amount of change of a nitrate to sulfate, the greater the increase in the electrical resistance R. Accordingly, the amount of trapped sulfur S, that is, the cumulative value of the amount of $SO_x$ in exhaust gas, can be found from the electrical resistance R.

FIG. 3(B) shows the detection part of the $SO_x$ sensor 5 shown in FIG. 1. As shown in FIG. 3(B), the detection part of the $SO_x$ sensor 5 arranged in the flow passage of the exhaust gas is provided with a metal compound piece for detection 12 supported by a pair of terminals 13 and a metal compound piece for reference 14 supported by a pair of terminals 15. The metal compound piece for detection 12 is formed from an oxide or carbonate or nitrate, while the metal compound piece for reference 14 is formed from a sulfate. If exhaust gas flows, the metal compound piece for reference 14 will not change, but if the metal compound piece for detection 12 is not a nitrate, it will change to a nitrate, then the $SO_x$ contained in the exhaust gas will cause the nitrate to gradually change into a sulfate. Therefore, the electrical resistance R of the metal compound piece for detection 12 will gradually increase.

The electrical resistance R of the metal compound piece for detection 12 will become higher when the temperature of the surroundings becomes higher. Accordingly, to eliminate the effects this temperature change has on the electrical resistance R, the metal compound piece for reference 14 is provided and the amount of trapped sulfur S is determined from the difference between the electrical resistance of the metal compound piece for detection 12 and the electrical resistance of the metal compound piece for reference 14 using a Wheatstone bridge as shown in FIG. 3(C), for example. When using a Wheatstone bridge as shown in FIG. 3(C), the voltage V appearing in a voltmeter 16 will, as shown in FIG. 3(D), decrease along with the increase of the trapped amount of sulfur S.

FIG. 4 shows a case where the measured electrical property is the permittivity or the electrostatic capacitance.

As shown in FIG. 4(A), if the amount of trapped sulfur S increases, that is, if the amount of change of a nitrate to sulfate increases, the relative permittivity rises and accordingly, the electrostatic capacitance C becomes larger. The detection part of the $SO_x$ sensor 5 in this case, as shown in FIG. 4(B), has a similar structure as the detection part of the $SO_x$ sensor 5 shown in FIG. 3(B). However, in the example shown in FIG. 4(B), it is formed into a structure where the terminals 13 and 15 can detect the electrostatic capacitances C of the corresponding metal compound pieces 12 and 14.

The electrostatic capacitances C of the metal compound pieces 12 and 14 can be measured using, for example, a charge/discharge circuit as shown in FIG. 4(C). That is, in FIG. 4(C), if connecting a switch 17 to a contact a to charge the metal compound piece for detection 12, then connecting the switch 17 to a contact b to discharge the metal compound piece for detection 12, a discharge current I as shown in FIG. 4(D) flows to an ammeter 19. If integrating this discharge current I, the integrated value will represent the electrostatic capacitance C.

Similarly, in FIG. 4(C), by connecting a switch 18 to a contact a to charge the metal compound piece for reference 14, then connecting the switch 18 to a contact b to discharge the metal compound piece for reference 14, it is possible to find the electrostatic capacitance C of the metal compound piece for reference 14. The electrostatic capacitance difference between the electrostatic capacitance C of the metal compound piece for detection 12 and the electrostatic capacitance C of the metal compound piece for reference 14 becomes smaller the more the amount of trapped sulfur S increases, thereby allowing the amount of trapped sulfur S to be found from this electrostatic capacitance difference.

Figure 5:
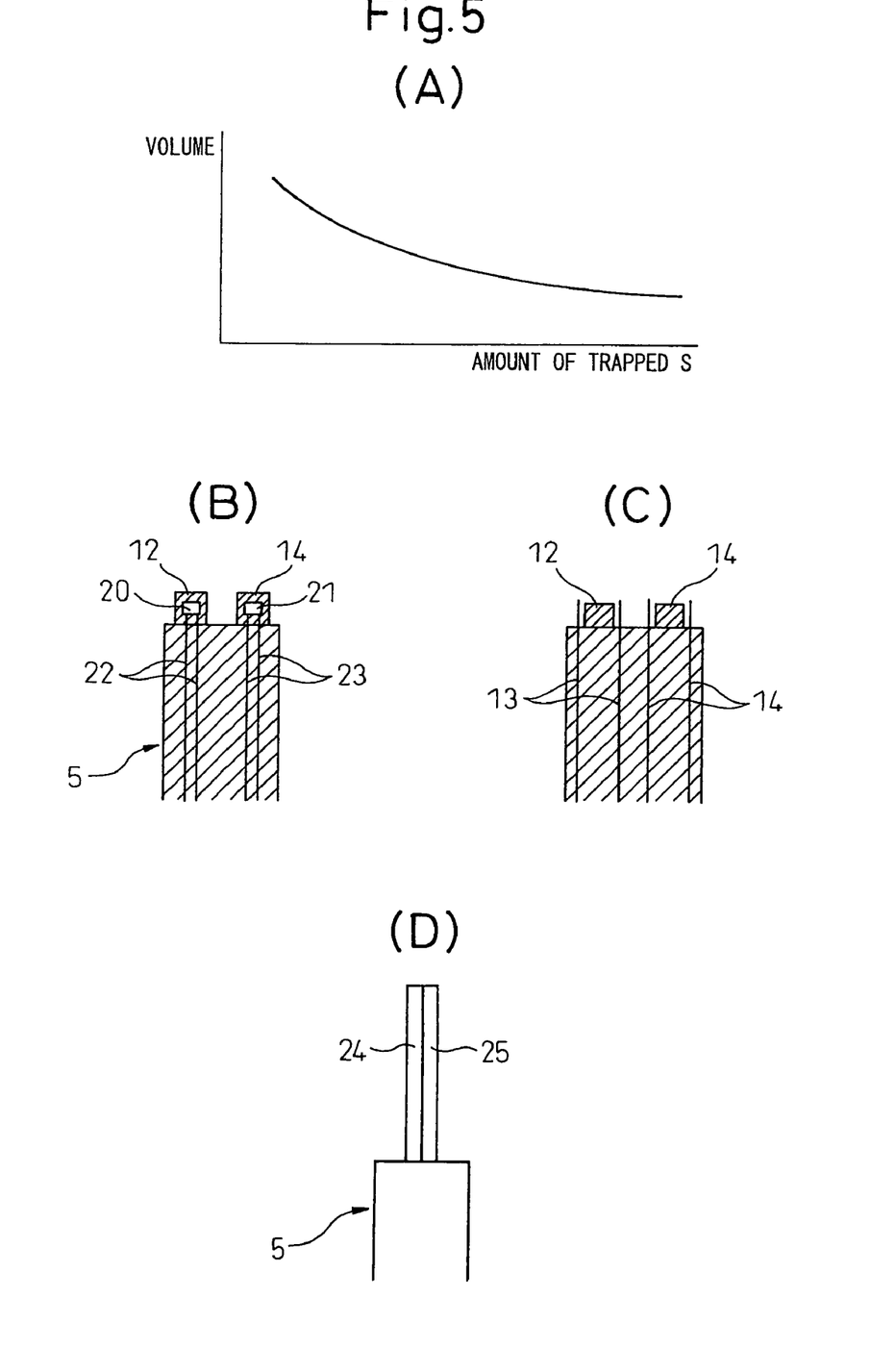
FIG. 5 is a view for explaining the method of detection of a sulfur component.

FIG. 5 shows a case where the measured property is a mechanical property and further shows a case where the measured mechanical property is a change in volume.

As shown in FIG. 5(A), the volume decreases the more the amount of trapped sulfur S increases. In FIGS. 5(B), (C), and (D), this change in volume is used to determine the amount of trapped sulfur S.

In the example shown in FIG. 5(B), the metal compound piece for detection 12 and metal compound piece for reference 14 are mounted on the detection part of the $SO_x$ sensor 5, while for example strain gauges 20 and 21 are mounted on the wall surface of the metal compound piece for detection 12 and the wall surface of the metal compound piece for reference 14 for detecting strains on each. Note that, in FIG. 5(B), reference numerals 22 and 23 show the lead wires of the strain gauges 20 and 21.

In this example, the strain of the metal compound piece for detection 12 is measured to measure the change in volume of the metal compound piece for detection 12, while the strain of the metal compound piece for reference 14 is measured to measure the change in volume of the metal compound piece for reference 14. The amount of trapped sulfur S may be determined from the difference of the measured changes in volume.

On the other hand, in the example shown in FIG. 5(C) as well, the metal compound piece for detection 12 and the metal compound piece for reference 14 are mounted on the detection part of the $SO_x$ sensor 5, but in this example, the change of the electrostatic capacitance due to the change in volume of the metal compound piece for detection 12 and the change in volume of the metal compound piece for reference 14 is detected.

In the example shown in FIG. 5(D), a bimetal element comprising a metal compound piece for detection 24 and a metal compound piece for reference 25 is mounted on the detection part of the $SO_x$ sensor 5. In this example, along with the increase of the amount of trapped sulfur S of the metal compound piece for detection 24, the amount of curvature of the bimetal element rises. Accordingly, the amount of trapped sulfur S can be determined from the size of the amount of curvature.

Figure 6:
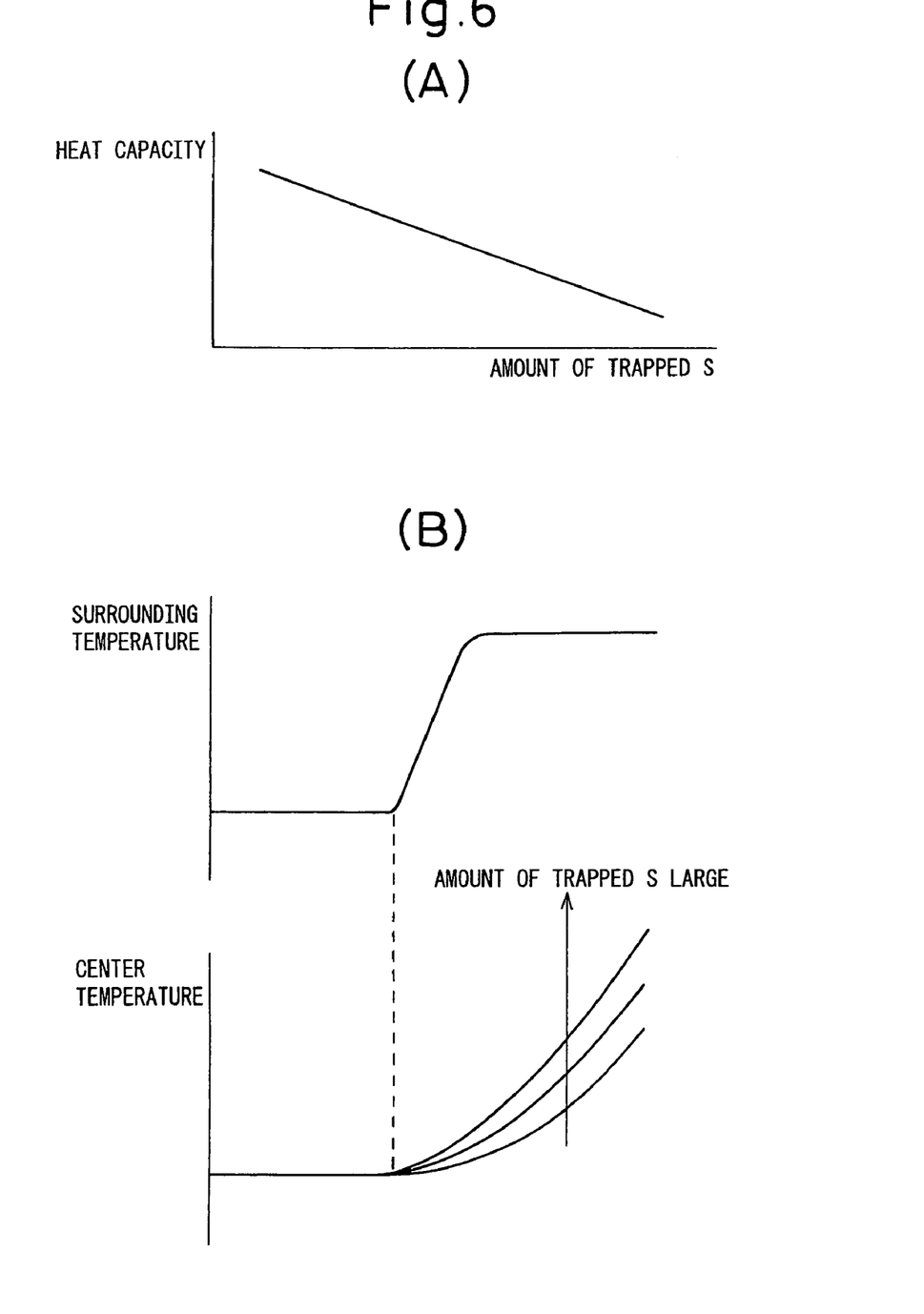
FIG. 6 is a view for explaining the method of detection of a sulfur component.
Figure 7:
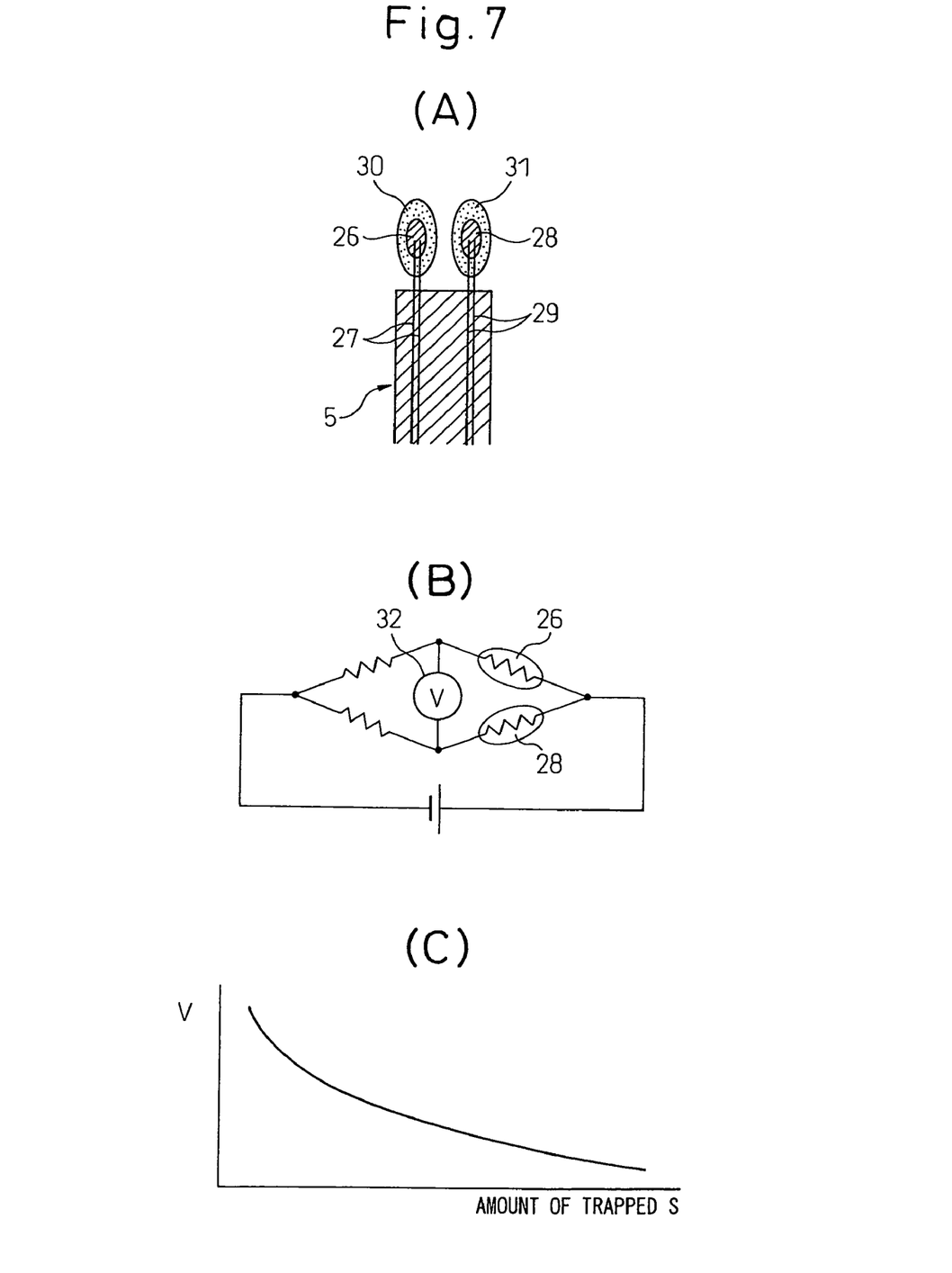
FIG. 7 is a view for explaining the method of detection of a sulfur component.
Figure 8:
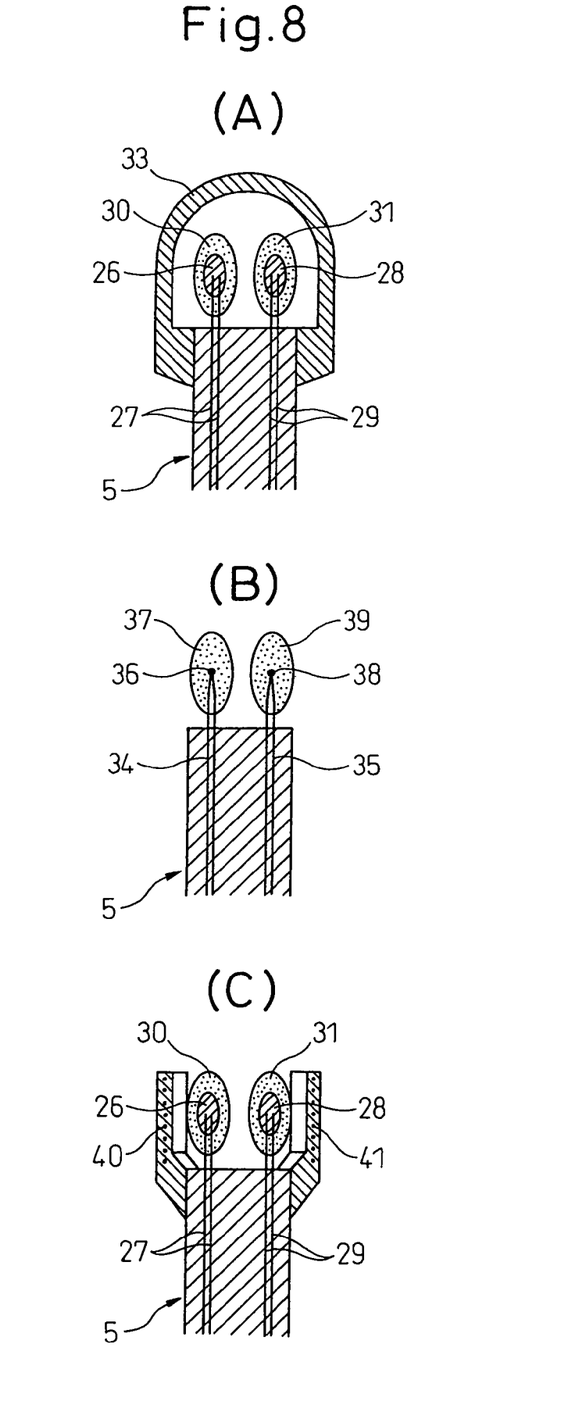
FIG. 8 is a view for explaining the method of detection of a sulfur component.

FIG. 6 to FIG. 8 show a case of where the measured property is a thermal property and further shows a case where the measured thermal property is a heat capacity and heat conductivity.

As shown in FIG. 6(A), the more the amount of trapped sulfur S increases, the more the heat capacity of the metal compound piece decreases. Accordingly, as shown in FIG. 6(B), when the surrounding temperature of the metal compound piece rises, the rate of increase of the center temperature of the metal compound piece rises the more the amount of trapped sulfur S increases.

FIG. 7(A) shows the detection part of the $SO_x$ sensor 5. In the example shown in FIG. 7(A), a thermistor element for detection 26 having a pair of lead wires 27 and a thermistor element for reference 28 having a pair of lead wires 29 are provided. Further, in this example, the surroundings of the thermistor element for detection 26 are surrounded by a metal compound for detection 30, and the surroundings of the thermistor element for reference 28 are surrounded by a metal compound for reference 31.

In this example, the heat capacity of the metal compound for detection 30 is estimated from the response of the change in the resistance of the thermistor element for detection 26 when the surrounding temperature of the metal compound for detection 30 has changed, while the heat capacity of the metal compound for reference 31 is estimated from the response of the change in the resistance of the thermistor element for reference 28 when the surrounding temperature of the metal compound for reference 31 has changed. The amount of trapped sulfur S is found from the difference of these heat capacities.

That is, specifically speaking, a Wheatstone bridge such as shown in FIG. 7(B) is used to find the difference between the resistance of the thermistor element for detection 26 and the resistance of the thermistor element for reference 28 in the form of voltage. In this case, the voltage V of the voltmeter 32 expressing the resistance difference falls, as shown in FIG. 7(C), the more the sulfur S trapped in the metal compound for detection 30 increases.

In the example shown in FIG. 8(A), the metal compound for detection 30 and the metal compound for reference 31 are covered by a porous cap 33 carrying an oxidation catalyst. If providing this cap 33, $SO_2$ and other sulfur compounds contained in the exhaust gas are oxidized to the trappable $SO_3$. This results in a rise in the trap rate of the sulfur component contained in the exhaust gas and thereby increases the detection accuracy of the sulfur component.

In the example shown in FIG. 8(B), the detection part of the $SO_x$ sensor 5 is provided with a thermocouple for detection 34 and a thermocouple for reference 35. In this example, the surroundings of temperature sensor contact points 36 of the thermocouple for detection 34 are surrounded by a metal compound for detection 37, while the surroundings of temperature sensor contact points 38 of the thermocouple for reference 35 are surrounded by a metal compound for reference 39. In this example, the heat capacity of the metal compound for detection 37 is estimated from the response of the change in the electromotive force of the thermocouple for detection 34 when the surrounding temperature of the metal compound for detection 37 has changed, while the heat capacity of the metal compound for reference 39 is estimated from the response of the change in the electromotive force of the thermocouple for reference 35 when the surrounding temperature of the metal compound for reference 39 has changed. The amount of trapped sulfur S is determined from the difference of these heat capacities.

Specifically, the amount of trapped sulfur S is found from the difference between the electromotive force of the thermocouple for detection 34 and the electromotive force of the thermocouple for reference 35.

In the example shown in FIG. 8(C), heaters 40 and 41 for heating the metal compound for detection 30 and the metal compound for reference 31 respectively are arranged. In this example, even if the surrounding temperature does not change, by making the heaters 40 and 41 generate heat, the difference between the heat capacities of the metal compound for detection 30 and the metal compound for reference 31 can be found.

Further, if the metal compound for detection 30 is made a high temperature, the metal compound for detection 30 releases the trapped $SO_x$ and therefore the metal compound for detection 30 is regenerated. Accordingly, in this example, the heater 40 is made to generate heat to make the temperature of the metal compound for detection 30 rise thereby enabling the regeneration of the metal compound for detection 30. Note that, in this case, even if making the air-fuel ratio of the exhaust gas temporarily rich, the metal compound for detection 30 can be regenerated.

Note that, in the case where the exhaust gas contains phosphorous P, both the sulfur S and phosphorous P are trapped, however, the amount of phosphorous P is small, so it is sufficient to find the amount of trapped sulfur S.

LIST OF REFERENCE NUMERALS

5 . . . $SO_x$ sensor
12 . . . metal compound piece for detection
14 . . . metal compound piece for reference
26 . . . thermistor element for detection
28 . . . thermistor element for reference
30 and 37 . . . metal compound for detection
31 and 38 . . . metal compound for reference
34 . . . thermocouple for detection
35 . . . thermocouple for reference

The invention claimed is:
1. A sulfur component detecting device for detecting a sulfur component contained in a flowing gas comprising:
a first metal compound for detection, wherein the first metal compound for detection is arranged in a gas flow passage and is able to trap a sulfur component in the gas, and as the amount of the sulfur component trapped at the first metal compound increases over time, a property of the first metal compound changes along with the increase in the amount of the trapped sulfur component to be measured, wherein the first metal compound for detection changes to a sulfate when trapping sulfur; and a second metal compound for reference arranged in the gas flow passage that is comprised of at least a sulfate;

the sulfur component in the gas is detected from a difference between the measured property of the first metal compound for detection and a measured property of the second metal compound for reference.

2. A sulfur component detecting device as claimed in claim 1, wherein the first metal compound comprises an oxide or carbonate or nitrate.

3. A sulfur component detecting device as claimed in claim 1, wherein said flowing gas is an exhaust gas exhausted from an internal combustion engine, and said sulfur component is $SO_x$ contained in the exhaust gas.

4. A sulfur component detecting device as claimed in claim 1, wherein said measured property of the first metal compound is an electrical property represented by electrical resistance and permittivity.

5. A sulfur component detecting device as claimed in claim 1, wherein said measured property of the first metal compound is a mechanical property represented by a change in volume.

6. A sulfur component detecting device as claimed in claim 1, wherein said measured property of the first metal compound is a thermal property represented by a heat capacity and heat conductivity.

7. A sulfur component detecting device as claimed in claim 1, wherein the measured property of the first metal compound is an electrical resistance of the first metal compound for detection.

8. A sulfur component detecting device as claimed in claim 1, wherein the measured property of the first metal compound is an electrostatic capacitance of the first metal compound for detection.

9. A sulfur component detecting device as claimed in claim 1, wherein the measured property of the first metal compound is a change in volume of the first metal compound for detection.

10. A sulfur component detecting device as claimed in claim 9, wherein the change in volume of the first metal compound for detection is measured by measuring a strain of the first metal compound for detection.

11. A sulfur component detecting device as claimed in claim 1, wherein the measured property of the first metal compound is an electrostatic capacitance changing due to a change in volume of the first metal compound for detection.

12. A sulfur component detecting device as claimed in claim 1, wherein the first metal compound for detection and the second metal compound for reference are covered by a porous cap carrying an oxidation catalyst.

13. A sulfur component detecting device as claimed in claim 1, wherein the measured property of the first metal compound is a heat capacity of the first metal compound for detection.

14. A sulfur component detecting device as claimed in claim 13, wherein surroundings of a thermistor element are surrounded by the first metal compound for detection, and the heat capacity of the first metal compound for detection is estimated from the response of a change in a resistance of the thermistor element when the surrounding temperature of the first metal compound for detection changes.

15. A sulfur component detecting device as claimed in claim 14, wherein in addition to the first metal compound for detection, the second metal compound for reference comprised of a sulfate is arranged in the gas flow passage, the surroundings of a thermistor element for reference is surrounded by the second metal compound for reference, and the sulfur component in the gas is detected from the difference between a resistance of the thermistor element arranged in the first metal compound for detection and a resistance of the thermistor element for reference.

16. A sulfur component detecting device as claimed in claim 15, wherein heaters for heating each of the first metal compound for detection and the second metal compound for reference are provided.

17. A sulfur component detecting device as claimed in claim 13, wherein surroundings of temperature sensor contact points of a thermocouple are surrounded by the first metal compound for detection, and a heat capacity of the first metal compound for detection is estimated from the response of a change in an electromotive force of the thermocouple when a temperature around of the first metal compound for detection changes.

18. A sulfur component detecting device as claimed in claim 17, wherein in addition to the first metal compound for detection, the second metal compound for reference comprised of a sulfate is arranged in the gas flow passage, surroundings of temperature sensor contact points of a thermocouple for reference are surrounded by the second metal compound for reference, and the sulfur component in the gas is detected from the difference between an electromotive force of the thermocouple where the temperature sensor contact points are arranged in the first metal compound for detection and an electromotive force of the thermocouple for reference.

19. A sulfur component detecting device as claimed in claim 18, wherein heaters for respectively heating the first metal compound for detection and the second metal compound for reference are provided.

20. A sulfur component detecting device as claimed in claim 1, wherein a cumulative amount of the sulfur component contained in the gas is detected from the difference between the measured property of the first metal compound for detection and the measured property of the second metal compound for reference.

21. A sulfur component detecting device as claimed in claim 1, wherein the first and second metal compounds arranged in the gas flow passage independently comprise compounds of an alkali metal, alkali earth metal, rare earth metal, or precious metal.

* * * * *